United States Patent
Yadav et al.

(10) Patent No.: US 6,204,424 B1
(45) Date of Patent: Mar. 20, 2001

(54) HIGHLY ACIDIC MESOPOROUS SYNERGISTIC SOLID CATALYST AND ITS APPLICATIONS

(75) Inventors: Ganapati Dadasahab Yadav, Mumbai; Munivemmal Sellamuthupillai Krishnan, Tamil Nadu; Nirav Shashikant Doshi; Ajit Atmaram Pujari, both of Mumbai; Mohamed Sheik Mohamed Mujeebur Rahuman, Tamil Nadu, all of (IN)

(73) Assignee: Secretary, Department of Science and Technology, Government of India (IN)

( * ) Notice: Subject to any disclaimer, the term of this patent is extended or adjusted under 35 U.S.C. 154(b) by 0 days.

(21) Appl. No.: 09/211,499

(22) Filed: Dec. 14, 1998

(30) Foreign Application Priority Data

Dec. 12, 1997 (IN) .............................. 3595/DEL/97
Dec. 12, 1997 (IN) .............................. 3590/DEL/97
Dec. 12, 1997 (IN) .............................. 3594/DEL/97

(51) Int. Cl.$^7$ .................................................. C07C 2/02
(52) U.S. Cl. .............................. 585/502; 502/60; 502/64; 564/305
(58) Field of Search ........................ 502/60, 64; 585/502; 564/305

(56) References Cited

U.S. PATENT DOCUMENTS 5,786,294 * 7/1998 Sachtler et al. ........................ 502/349
5,811,614 * 9/1998 Acholla et al. ........................ 585/467

\* cited by examiner

*Primary Examiner*—Tom Dunn
(74) *Attorney, Agent, or Firm*—Pendorf & Cutliff

(57) ABSTRACT

An eco-friendly synergistic heterogeneous solid catalyst for use in reactions such as alkylation, acylation, oligomerization, isomerization, hydration, dehydration, etherification, esterification, hydrocracking and nitration of organic compounds comprising:

a synergistic combination of sulfated metal oxide and mesoporous zeotypes comprising:

Silicon (Si) 50–60 wt %, Zirconium (Zr) 40–50 wt %, Sulfur (S) 5–10 wt % and having
a surface area in the range of 200–500 m$^2$/g;
a pore volume in the range of 0.1–0.3 m$^3$/g;
a pore diameter in the range of 25–35 Å; and
a XRD peak at 2θ being 0–3.

The invention also covers the process of manufacture of the above catalysts and its use in particular for producing oligomers from alpha-olefins, Friedel-Crafts alkylation and acylation reactions.

25 Claims, No Drawings

HIGHLY ACIDIC MESOPOROUS SYNERGISTIC SOLID CATALYST AND ITS APPLICATIONS

BACKGROUND OF THE INVENTION

1. Field of the Invention

This invention relates to a new eco-friendly heterogeneous solid catalyst for use in reactions such as alkylation, acylation, olegomerization, isomerization, hydration, dehydration, etherification, esterification, hydrocracking and nitration of organic compounds for expected shape selectivity in mesoporous range and its method of manufacture. The catalyst of the present investigation is in the field of sulphated zirconia and mesoporous molecular sieves.

2. Description of the Related Art

Zeolites are the important family of solid acid catalysts having tridimentional crystalline aluminosilicate network with channels and cavities of molecular dimensions. The system of these molecular sieves produces materials with very high surface area and pore volume, which are capable of adsorbing great amounts of organic molecules. There has been, however, an ever growing interest in expanding the pore sizes of molecular sieve materials from the micropore region to mesopore region in response to the increasing demands in both industrial and fundamental studies. Mesoporous zeotype materials are inherently poor stability and weakly acidic.

In 1992, researchers at Mobil Corporation discovered the M41S family of silicate/aluminosilicate mesoporous molecular sieves with exceptionally large uniform pore structure (Kresge, C. T.; et al. *Nature* 1992, 359, 710–712, Beck, J. S.; et al. *J. Am. Chem. Soc.* 1992, 114, 10834–10843). This has resulted in a world-wide resurgence in this area. The template agent used is no longer a single, solvated organic molecule or metal ion, but rather a self-assembled surfactant molecular arrays. The mesoporous material synthesised in the above method possesses highly regular arrays of uniform-sized channels whose diameters are in the range of 15–100 Å depending on the templates used, the addition of auxiliary organic compounds, and the reaction parameters.

Synthesis of mesoporous materials have been reviewed by Tanav, P. T. and Pinnavaia, T. J. (*Science*, 267, 865–867) There are four general methods of preparation of mesoporous materials and any one could be used to synthesize them in the laboratory.

The first three routes are based on ionic mechanisms while the fourth employs neutral templates to prepare hexagonal mesoporous molecular sieves (HMS). The last (IVth) route is based on the self-assembly between neutral primary amine micelles ($S^\circ$) and neutral inorganic precursor ($I^\circ$). This neutral $S^\circ I^\circ$ produces mesostructures with larger wall thickness and complementary textural mesoporosities vis-a-vis those materials produced by routes I to III. The thicker pore walls improve the thermal and hydrothermal stability of the mesoporous framework. The $S^\circ I^\circ$ pathway also allows for the facile recovery of the template by simple solvent extraction.

From the above literature it can be concluded that, the preparation of mesoporous material using the neutral templating method provide a better approach to get mesoporous materials. But, they too have the disadvantage of having very low acidity compared with other solid acid catalysts particularly for reaction requiring high acidity. With the possibility to generate active sites inside of the channels and cavities of zeolites and zeotypes, a very unique type of shape selective catalyst may be produced and it can be visualised as a microreactor. Therefore, any modification which can promote the surface acidity along with their molecular sieving property of these catalysts will be highly desirable.

On the other hand, catalysts based on zirconia and other metal oxides showed very high acidity and activity when small amount of sulphate was treated with them. Hino and Arata (Hino, M.; Arata, K. J. *Chem. Soc., Chem. Commun.*, 1980, 851–852) have reported that sulphated zirconia is an acid $10^4$ times stronger than 100% sulphuric acid and with the Hammett acidity function—$H_0=16$, it is considered as the strongest halide-free solid superacid ever reported. The strong acidity makes it attractive as a catalyst in many organic reactions such as alkylation, acylation, isomerization, etherification, esterification, hydration, dehydration, olegomerization, hydrocracking, etc. However, these superacidic materials have not found many applications because of their low surface area and non-shape selective nature. Developing a process for super acidic modified metal oxide catalyst with a high surface area along with molecular sieving property is a challenging field to researchers. This will have applications in heavy oil cracking and pharmaceuticals involving bulky structures.

Different approaches to introduce (a) strong acidic centres into molecular sieve materials and (b) shape selectivity into sulphate promoted metal oxide catalysts revealed that by introducing the shape selectivity into the oxide materials the surface area increases considerably. However, the desired activity and selectivity could not be achieved in either case. Nor was it possible to provide the catalyst having desired activity by loading the superacids on the molecular sieve material.

SUMMARY OF THE INVENTION

It is the basic objective of the present invention to provide an ecofriendly heterogeneous solid catalyst possessing high surface area, high acidity and mesoporosity for use in catalysed organic reactions with high selectivity/specificity such as alkylation, acylation, olegomerization, isomerization, hydration, dehydration, etherification, esterification, hydrocracking and nitration of organic compounds.

Another object of the present invention is directed to a process for producing the aforesaid ecofriendly heterogeneous solid catalyst possessing high surface area, high acidity and mesoporosity for use in catalysed organic reactions with high selectivity/specificity.

Yet further object of the present invention is directed to providing for a synergistic heterogeneous solid catalyst having combination of the benefits of superacids such as sulphated metal oxide and mesoporous molecular sieve to achieve the desired catalytic activity and selectivity.

Another objective of the present invention to provide a process for oligomerization of alpha olefins with carbon numbers $C_6$–$C_{16}$ to obtain an oligomer with two monomer units or molecule as the major product so that the problem of separation by distillation from higher oligomers can be eliminated.

Another object of this invention is to provide for pure dimers by using pure monomers.

Yet another objective of the present invention is to provide a process for carrying out Friedel-Crafts reactions strongly corrosive acidic catalysts which would avoid the drawbacks associated with presently known catalysts used in such reactions discussed herein before.

Another object of the present invention is to provide a process for carrying out Friedel-Crafts reaction using strongly corrosive acidic catalysts which would be free of catalyst disposed problems associated with the known art.

Yet further object of the present invention is directed to a process for Friedel-Crafts reaction which would provide for better yield as compared to known processes of Friedel-Crafts reaction.

Thus according to one aspect of the present invention there is provided a highly acidic mesoporous synergistic solid catalyst comprising hexagonal mesoporous silica having sulphated metal oxide of metal selected from the group consisting of zirconium, titanium, iron, aluminium, tin and bismuth incorporated therein and having a surface area in the range 200–500 m$^2$/g; a pore volume in the range of 0.1–0.3 ml/g; a pore diameter in the range of 25–35 Å amd XRD peak at 2 theta angle being 0–3.

Preferably, the highly acidic mesoporous synergistic solid catalyst is provided to have an elemental constitution of Silicon (Si) 50–60 wt %, zirconium (Zr) 40–50 wt % and Sulphur (S) 5–10 wt %.

The above disclosed highly acidic, mesoporous synergistic solid catalyst of the invention is found to have desirable properties for carrying out catalysed organic reactions with high selectivity/specificity.

According to the present invention there is provided a process for the preparation of a highly acidic mesoporous solid catalyst "UDCaT-1" (University Department of Chemical Technology, University of Mumbai) by forming in situ deposition of a metal hydroxide in a mesoporous molecular sieve (HMS) and then promoting its acidity by sulphating agents.

According to another aspect of the present invention there is provided a process for the preparation of a highly acidic mesoporous synergistic solid catalyst comprising the steps of:

(i) depositing water soluble salts of metals in an amount of 0.1–5.0 parts by weight into hexagonal mesoporous silica (HMS) with a pore size 13 Å in an amount of 1–10 parts by weight;

(ii) passing ammonia gas over the metal salt deposited HMS and thereby converting the metal salt deposits in the HMS to metal hydroxide deposits in HMS, followed by washing and drying either under vacuum at 50–100° C. or at 100–150° C. at atmospheric pressure;

(iii) sulphating the metal hydroxide deposits in the HMS with at least one sulphating agent; and (iv) calcining the sulphated, metal deposited HMS between 400–700° C. to thereby obtain the said catalyst.

In the above disclosed process of the invention the water soluble salts of metals are selected such as from the group of Zirconium, Titanium, Iron, Aluminium, Tin and Bismuth.

The sulphating agents suitable for use in the above process of the invention include sulphuric acid, ammonium sulphate, sulphur dioxide, sulphur trioxide and hydrogen sulphide.

The preferred mesoporous molecular sieve (HMS) is one prepared from alkoxide of silicon with primary amine as a template, the said primary amine having carbon atoms from 8 to 16.

The mesoporous molecular sieve (HMS) is one prepared from alkoxide of silicon with primary amine as a template.

The preferred metal salt used for the deposition on HMS is zirconium oxychloride.

The HMS carrying metal hydroxide is sulphated by passing preferred sulphating agent, dilute sulphuric acid, 15 ml/g (0.1 to 5.0 N) over the dried ammoniated solid material placed on a filter medium.

The HMS carrying metal hydroxide may also be sulphated by another sulphating agent aqueous ammonium sulphate.

The sulphated HMS carrying metal hydroxide is calcined preferably between 500–700° C.

In particular, the process of invention, the HMS (one part by wt.) is taken in a reactor and the solution of metal salt (0.1–5 parts by wt.) preferably (0.5–1 parts by wt.) is added in dropwise under vigorous mixing by the incipient wetness method. The metal salt containing HMS is dried.

Materials prepared by any route having mesoporous structure with pore size >13 Å such as MCM-41 can be used.

Any water soluble metal salt(s) selected from the group Zirconium, Titanium, Iron, Aluminium, Tin and Bismuth may be used.

The dried metal salt containing HMS is taken in a vertical vapour phase reactor and ammonia gas is passed through it for 1–3 h. It is dried at 80–150° C. for 1–3 h to get the metal hydroxide deposited HMS.

The sulphation of the metal hydroxide deposited HMS (the solid material) is carried out by treatment with sulphating agents such as sulphuric acid, ammonium sulphate, sulphur dioxide, sulphur trioxide and hydrogen sulphide either in solution or in gaseous phase as appropriate, preferably sulphuric acid and ammonium sulphate.

The sulphated metal deposited HMS is then dried at temperature between 100° C. and 150° C. and calcined at a temperature between 400° C. and 750° C. preferably between 500° C. and 650° C.

In one embodiment of the process of invention, HMS is prepared by the following procedure. A primary amine ($C_8$–$C_{16}$) used as the template (one part) is dissolved in a solvent such as aqueous alcohol ($C_1$–$C_3$) mixture (1:1–1:5). An alkoxide of silicon such as tetraethyl orthosilicate was added under vigorous stirring. The reaction mixture was allowed for aging for 5–30 h at temperature up to 100° C. The precipitate is separated, and dried, and calcined at a temperature between 400° C. and 800° C., preferably between 500° C. and 700° C. to form the HMS.

In an another embodiment of this HMS preparation process, the template is extracted instead of calcining, as follows.

The precipitate (1 part) as prepared by following the procedure given in the above paragraph, is dried and extracted with a solvent preferably any alcohol ($C_1$–$C_3$), 8–15 parts, under reflux to obtain the HMS. It is dried at 80–150° C. The template recovered from the extract is preserved for reuse.

In another embodiment of the process of invention, use of sulphuric acid as a sulphating agent is preferred. In this case 8–20 ml of dilute sulphuric acid (1–2N) is stirred with each gram of the solid material and the solid is separated by filtration, dried at 100–150° C. and calcined at 400–700° C., preferably at 500–650° C.

In accordance with another aspect of the present invention there is provided a process for producing oligomers from alpha-olefins comprising:

contacting alpha olefin feedstock, $RCH\!=\!CH_2$ wherein R represents an alkyl radical having 6 to 12 carbon numbers, with a sulphated metal oxide molecular sieve catalyst such as herein before described;

adding 1 to 10% by weight of alpha olefin, under agitation;

raising the temperature to 120 to 220° C., appropriate to the hydrocarbon(s) in the feedstock and maintaining the reaction at that temperature under agitations for a period between 2 to 10 hours under pressure;

cooling the reactant to room temperature and separating the solid catalyst from the liquid products of the reaction followed by separating the unreacted monomer and the oligomer.

In accordance with yet another aspect of the present invention there is provided.

A process for Friedel-Crafts reactions comprising:

i. contacting aromatic compounds with acylating/alkylating agents in presence of highly acidic mesoporous solid catalyst such as herein before described;

ii. maintaining the reaction under stirring at the reaction temp 50–100° C. from 30 mins to 6 hours; and iii. recovering the reaction product by conventional methods.

DETAILED DESCRIPTION OF THE INVENTION

EXAMPLES

The invention is now described hereunder in greater detail by way of examples given below which are provided by way of illustration only of some preferred embodiments and should not be constructed to limit the scope of the present invention.

I. PREPARATION OF HIGHLY ACIDIC MESOPOROUS SOLID CATALYST

Example-1

The hexagonal mesoporous silicate (HMS) was prepared with following procedure. 5 g Dodecyl amine was dissolved in 41.8 g of ethanol and 29.6 g of distilled water. 20.8 g of tetraethyl orthosilicate was added under vigorous stirring to it. The addition of ethanol improved the solubility of the template. The reaction mixture was aged for 18 hours at 30° C. The clear liquid above the white coloured precipitate was decanted and the precipitate HMS, was dried on a glass plate. The template was removed either by calcining the resulting material at 550° C. in air for 3 h or by refluxing the dried HMS material twice in 150 ml ethanol for 1 h and drying it at 80° C. in an oven for 2 h.

2.5 g zirconium oxychloride dissolved in 10 ml of distilled water was added in drops to the 5 g of calcined HMS with vigorous mixing. Special precaution was taken during the said procedure of addition of aqueous solution of zirconium oxychloride in calcined HMS. After very little addition of the solution, the solid was partially dried over a boiling water bath. Ultimately, after all the addition was over, the solids were dried in an oven at 120° C. for 1 h. The dried material was loaded in a reactor and ammonia gas was passed through it for 3 h. The ammoniated sample was washed with distilled water to remove the chloride ions and dried in oven at 120° C. for 2 h. The sulphation was done by passing 1N sulphuric acid (15 ml/g) through the filter paper containing the dried ammoniated solid material. It was dried in oven for 1 h at 120° C. and calcined at 550° C. for 3 h to give the active catalyst UDCaT-1(i).

Catalyst prepared by process of example 1 was found to be useful in Friedel-Crafts reaction and in oligomerisation of alpha olefins.

Example 2

The process of example 1 was repeated up to the stage of preparation of zirconium hydroxide in situ in HMS and then sulphation of the dried ammoniated solid material was done by using 2.5 g ammonium sulphate in 6 ml distilled water instead of sulphuric acid in the sulphation step. In this case sulphation was done by wetting the dried ammoniated solid material in the ammonium sulphate solution by incipient wetness method. The sulphated material was then dried in an oven for 1 h at 120° C. and calcined at 550° C. for 3 h. This gave the active catalyst UDCaT-1(ii).

Characterisation of the catalyst prepared by the process of the present investigation The characteristics of the catalyst UDCaT-1(i and ii) were examined by measuring its, surface area, pore volume, pore diameter, x-ray diffraction, FT-IR and elemental analysis by standard procedures. The results are tabulated below in TABLE 1A–1D.

TABLE 1A

Nitrogen adsorption data: (1) Surface area

| Catalyst | Single point surface area m$^2$/g | Langmuir surface area m$^2$/g | BJH adsorption cumulative surface area m$^2$/g | BJH desorption cumulative surface area m$^2$/g |
|---|---|---|---|---|
| HMS | 858.56 | 865.56 | 1170.10 | 1182.71 |
| UDCaT-1 (i) | 403.26 | 411.14 | 358.99 | 316.86 |
| UDCaT-1 (ii) | 265.82 | 275.70 | 272.37 | 250.42 |
| SO$_4^{-2}$—ZrO$_2$ | 100.45 | 105.41 | 114.75 | 135.43 |

* ASAP 2010 V3.00, Analysis Adsorptive: N$_2$, Analysis Bath: 77.30K, Low Pressure Dose: 5 cm$^2$/g STP, Equilibrium Interval: 20 secs., Sample Weight: 0.2 g.

TABLE 1B (2) Pore volume

| Catalyst | Single point total pore volume m$^3$/g | BJH adsorption cumulative pore volume m$^3$/g | BJH desorption cumulative pore volume m$^3$/g |
|---|---|---|---|
| HMS | 0.7885 | 0.6848 | 0.6907 |
| UDCaT-1 (i) | 0.2919 | 0.2174 | 0.1991 |
| UDCaT-1 (ii) | 0.2122 | 0.1755 | 0.1702 |
| SO$_4^{-2}$—ZrO$_2$ | 0.1079 | 0.1088 | 0.1334 |

* ASAP 2010 V3.00, Analysis Adsorptive: N$_2$, Analysis Bath: 77.30K, Low Pressure Dose: 5 cm$^2$/g STP, Equilibrium Interval: 20 secs., Sample Weight: 0.2g.

TABLE 1C (3) Pore Diameter (Å)

| Catalyst | Average pore diameter (4V/A by Langmuir) | BJH adsorption average pore diameter (4V/A) Å | BJH desorption average pore diameter (4V/A) Å |
|---|---|---|---|
| HMS | 36.44 | 23.41 | 23.36 |
| UDCaT-1 (i) | 28.40 | 24.23 | 25.13 |
| UDCaT-1 (ii) | 30.79 | 25.78 | 27.18 |
| SO$_4^{-2}$—ZrO$_2$ | 40.93 | 37.92 | 39.40 |

* ASAP 2010 V3.00, Analysis Adsorptive: N$_2$, Analysis Bath: 77.30K, Low Pressure Dose: 5 cm$^2$/g STP, Equilibrium Interval: 20 secs., Sample Weight: 0.2g.

TABLE 1D

Elemental Analysis[+]: UDCaT-1 (ii)

| Element & Line | Weight Percent | Atomic Percent | Precision 2 sigma | K-Ratio[**] | Item |
|---|---|---|---|---|---|
| Si KA | 51.41 | 72.83 | 1.93 | 0.5840 | |
| S KA | 7.43 | 9.22 | 0.96 | 0.0684 | |
| Zr LA | 41.16 | 17.95 | 3.64 | 0.3475 | 2 |

Note: Accelerating Voltage: 10.0 Kev, Incidence Angle: 90° C., X-Ray Emergence Angle: 62° C.
[+](Standardless EDS Analysis, ZAF corrections via Magic V),
[*]Atomic Percent is normalized to 100,
[**]K-Ratio = K-Ratio × R (where R = reference (standard)/reference (sample), Normalization Factor: 0.925, To summarise,
The catalyst UDCaT-1 characteristics show the

| surface area | 200–500 m$^2$/g |
|---|---|
| pore volume | 0.1–0.3 m$^3$/g |
| pore diameter | 25–35 Å |
| XRD (2θ) | 0–3° |

Elemental analysis

| Element | Wt % |
|---|---|
| Si | 50–60 |
| S | 5–10 |
| Zr | 40–50 |

The Catalytic activity

II. The catalytic activity of the catalyst UDCaT-1(i) prepared in accordance with the present invention was tested by use in the process of oligomerization of alpha olefins discussed in the following examples:

Example 3

Process for Dimerization of 1-decene

Materials
1-decene was obtained from Albemarle Corp., USA. Catalyst UDCat-1 is obtained as disclosed under Examples 1 and 2 and the catalyst used in the Examples 3 and 5 were prepared as described under Examples 1 and 2 above and that of Examples 6 and 7 were prepared by conventional method. Whereas DTP and K10 were obtained from a reputed firm.

Apparatus:
Parr autoclave
All experiments were carried out in 100 ml stainless steel Parr autoclave. A pitched four bladed turbine impeller was used for agitation.

Process:
36 gm of 1-decene, 2.5 gm UDCaT-1 catalyst were charged into autoclave and the temperature was raised to desired 190° C. and speed of agitation was maintained at 800 rpm under autogeneous pressure for 4 hrs.

The autoclave was cooled to room temperature and then the catalyst was separated by filtration by using a Buchner funnel. The catalyst was washed with acetone and calcined at 650° C. for 3 hrs and preserved for reuse.

Filtrate showed only two peaks viz, monomer and dimer on GLC as per detail given in chart-1.

The monomer was separated by distillation at 130° C. under vacuum (200 mm of Hg) and weighed 18 gm. This was preserved for reuse. The second fraction distilled out at 160° C. under vacuum (200 mm of Hg) was of dimer and weighed 18 gm. There were no polymers left in the still.

Analysis of the dimer fraction.

Dimer was analysed by GC and its molecular weight was confirmed by GC-MS and both analysis show that dimer fraction is 100% pure dimer.

Chart-1 Details of GLC.

Analysis of the sample was done by using a gas chromatograph (Perkin-Elmer 8500) with a flame ionisation detector. The products were analysed for 1-decene, dimer and trimer.

| Column | Stainless steel. |
|---|---|
| Stationary phase | 10% OV-17 supported on chromosorb WHP |
| Dimensions | 2 Mt. length × 0.003 m dia |

Conditions:

| Carrier gas | nitrogen |
|---|---|
| Carrier flow rate | 30 ml/min |
| Injector | 300° C. |
| Detector | 300° C. |
| Oven temperature conditions: | |
| Temperature 1 | 150° C./1 min |
| Ramp 1 | 30° C./min |
| Temperature 2 | 300° C./10 min |

Example 4

Hydrogenation:

The dimer fraction obtained in the Example 3 was hydrogenated over nickel catalyst at 150° C. to give hydrogenated lubricant product. The viscosity of hydrogenated 1-decene dimer as shown in Table-4. It was found to be acceptable/comparable to other commercial product.

TABLE 2

Viscosity of hydrogenated 1-decene dimers

| | Viscosity in centistokes (cSt) | |
|---|---|---|
| Temperature | Product (dimer)[+] | commercial product[*] |
| 100° C. | 2.22 | 1.80 |
| 40° C. | 6.0 | 5.54 |
| −18° C. | 60 | 62 |

[*](DURASYN 162, Albemarle Corp, USA).
[+]method used ASTM D KV 445

Pour point and viscosity index were measured (ASTM D 2270, 1298) and it were found to be −60° C. and 99 respectively compared to −65° C. and 97 of the authentic dimer (DURASYN 162, Albemarle Corp, USA).

Examples 5–9

In these Examples the procedure of Example 3 was repeated replacing the UDCaT-1 catalyst by other solid acid catalysts as shown in Table-5. Product distribution of the different oligomers found by GC on 10% OV-17 on chromosorb WHB are given in Table-3, for comparison results of Example-3 are also included.

TABLE 3

| Example no | Catalyst used | Yield % of oligomers | % oligomers in the product | | |
|---|---|---|---|---|---|
| | | | Dimer | Trimer | Tetramer |
| 3. | UDCat-1 | 50 | 100 | — | — |
| 5. | HMS | 0 | 0 | 0 | 0 |
| 6. | S—ZrO | 23 | 95 | 5 | — |
| 7. | Al pillared Clay | 16 | 90 | 10 | — |
| 8. | DTP | 8 | 100 | — | — |
| 9. | K10 montmorillonite clay | 73 | 88 | 12 | — |

DTP: Dodecatungstophosphoric acid

The catalysts used in the Examples 3 and 5 were prepared as discussed above. Examples 6 and 7 were prepared by conventional method. Whereas DTP and K10 were obtained from a reputed firm.

As can be seen from the Table-3 that HMS is not at all effective under these conditions and all the other catalysts used give the mixture of oligomers. In the presence of K10 montmorillonite catalyst selectivity towards dimer formation is higher at 88. UDCat-1 catalyst alone gives 100% selectivity towards dimer formation, thereby making it easy to recycle the unreacted monomer (50%).

Examples 10 and 11

In these examples other olefins like 1-octene and 1-dodecene were also oligomerized as per the procedure given in Example-3 and the results obtained are shown in Table-4.

TABLE 4

Oligomerization of 1-octene and 1-dodecene using UDCaT-1 catalyst.

| Example No. | Alpha olefin | Yield % | % of oligomers formed | | |
|---|---|---|---|---|---|
| | | | Dimer | Trimer | Tetramer |
| 10. | 1-Octene | 50 | 100 | — | — |
| 11. | 1-Dodecene | 45 | 100 | — | — |

Example 12

In this example mixture of two pure monomers viz. olefin 1-octene and 1-decene (50:50 % by wt/wt) were oligomerised as per the procedure given in Example 3 and the results obtained are given in Table-5

TABLE 5

Oligomerization of mixture of 1-octene and 1-decene using UDCaT-1 catalyst.

| Example No | Alpha olefin | % conversion of $C_8$ | % conversion of $C_{10}$ | % Oligomers formed | |
|---|---|---|---|---|---|
| | | | | Dimer ($C_8$) | Dimer ($C_{10}$) |
| 12 | 1-octene + 1-decene 1:1 mol | 50 | 45 | 100 | 100 |

It was found that there was no trimer of 1-octene or 1-decene formed. Absence of octadecene($C_{18}$) in the reaction product showed that there was no reaction between 1-octene and 1-decene.

These examples show that the process of oligomerization of the present invention controls oligomerization to the dimer stage.

Further, the monomer could be distilled out and reused. In a continuous process, monomer could be recycled. Catalyst can be regenerated and used again and again.

III. The catalytic activity of the catalyst UDCaT-1(i) prepared in accordance with the present invention was tested by use in the process of Friedel-Crafts agitation process discussed in the following examples:

Example 13

Acylation of benzene with 4-chloro benzoyl chloride in presence of Aluminium chloride.

i. Acylation of benzene with 4-chloro benzoyl chloride in presence of Aluminium chloride.

The current industrial processes employs aluminum chloride. The reaction has a drawback of being homogeneous and hence the problem of recovery of the catalyst. Besides, the amount of the catalyst used is equimolar to the amount of reactant which is very high. 90% conversion of 4-chlorobenzoyl chloride to 4-chlorobenzophenone takes place in 4 h at 65–70° C. Reported reaction yield is 70%.

ii. Tanabe K. and Yamaguch et al., have reported the reaction by using heterogeneous catalyst such as sulphated zirconia to overcome the difficulty in disposal of used catalyst in this reaction.

In this case, though the catalyst could be separated out after the reaction its regeneration for reuse was difficult.

Catalysts and Chemicals

Aluminium chloride and benzene was obtained from S.D. Fine Chem Ltd. 4-chlorobenzoyl chloride was obtained from Merck (India) Ltd. All the chemicals were analytical grade and were used without further purification.

Preparation of UDCaT-1:

5 g Dodecyl amine was dissolved in 41.8 g of ethanol and 29.6 g of distilled water. 20.8 g of tetraethyl orthosilicate was added under vigorous stirring to it. The addition of ethanol improved the solubility of the template. The reaction mixture was kept for aging for 18 hours at 30° C. The clear liquid above the white coloured precipitate was decanted and the precipitate HMS, was dried on a glass plate. The template was removed either by calcining the resulting material at 550° C. in air for 3 h or by refluxing the dried HMS material twice in 150 ml ethanol for 1 h and drying it at 80° C. in an oven for 2 h.

2.5 g Zirconium oxychloride dissolved in 10 ml of distilled water was added in drops to the 5 g of calcined HMS with vigorous mixing. Special precaution was taken during the said procedure of adding aqueous solution of zirconium oxychloride in calcined HMS. After every little addition of the solution, the solid was partially dried over a boiling water bath. Ultimately, after all the addition was over, the solids were dried in an oven at 120° C. for 1 h. The dried material was loaded in a reactor and ammonia gas was passed through it for 3 h. The ammoniated sample was washed with distilled water to remove the chloride ions and dried in an oven at 120° C. for 2 h. The sulphation was done by passing 1N sulphuric acid (15 ml/g) through the filter paper containing the dried ammoniated solid material. It was then dried in an oven for 1 h at 120° C. and calcined at 550° C. for 3 h to give the active catalyst UDCaT-1.

Experimental setup

The reactor consisted of a flat glass vessel of 5 cm i.d., 10 cm height and 150 ml of capacity equipped with baffles and a six blade impeller. The assembly was kept in an oil bath at 65–70° C. The reaction mixture could be agitated at the required speed with the help of a variable motor.

Reaction procedure 4-chloro benzoyl chloride (0.02 moles) and benzene (0.2 moles) were fed into the reactor. Catalyst (0.02 moles) was added to the reaction mixture and the reaction mixture was heated at reflux temperature. An initial sample was then drawn and the agitation started. The reaction was monitored by periodic withdrawal of samples.

The samples were analysed on HPLC (Model:Toscho, UV-8010) by using C18 supported on silica column. Mobile phase methanol and water (60:40) were used for analysis of the samples. The quantitative analysis was done by comparison with standard synthetic mixtures.

After 5 hrs, benzene was removed by distillation and reaction mixture was poured into water which contained dil.hydrochloric acid to neutralise the mixture.

Results

Conversion and yield are given in Table 6.

Examples 14–22

Acylation of benzene with 4-chloro benzoyl chloride using catalysts other than aluminium chloride.

Catalysts and Chemicals

Amberlyst-15 and Amberlite IR 120 were obtained from Rohm and Hass. K-10 was a montmorillonite clay obtained from Fluka and Filtrol-24 clay was obtained from Engelhard. Indion 130 was obtained from Ion Exchange (India) Ltd. Dodecatungstophosphoric acid and benzene was obtained from MIS. S.D. Fine chemicals Ltd. Sulphated zirconia was prepared in our lab. UDCaT-1 as described in Example 12. A bitransitional metal halide constituting of ferric chloride and aluminium chloride, HPA supported on K-10 were used. Aluminium chloride and ferric chloride supported in the ration of 0:1, 1:3, 3:1, 1:0 were also sued. UDCaT-1 was prepared as described under Example 13. 4-chlorobenzoyl chloride were obtained from Merck Ltd. The catalysts used for the reaction were dried at 100° C. under vacuum for 6 hr. before use.

All the chemicals were analytical grade and were used without further purification.

Experimental setup

The reactor consisted of a flat glass vessel of 5 cm i.d., 10 cm height and 150 ml of capacity equipped with baffles and a six blade impeller. The assembly was kept in a oil bath at 65– 70° C. The reaction mixture could be agitated at the required speed with the help of a controllable motor.

Reaction procedure 4-chloro benzoyl chloride (0.02 moles) and benzene (0.2 moles) were fed into the reactor. A catalyst (10% w/w) as shown in Table 6, was added to the reaction mixture and the reactor was heated to 70° C. and maintained at 70±1° C. An initial sample was then withdrawn and the agitation started. The reaction was monitored by periodic withdrawal of samples.

The samples were analysed on HPLC (Model:Toscho, UV-8010) by using C18 supported on silica column. A mobile phase methanol:water (60:40) were used for analysis of the samples. The quantitative analysis was done by comparison with standard synthetic mixtures.

After 4 hrs, when the reaction was complete and the product was isolated by distilling the excess quantity of benzene.

Results:

The conversion of 4-chlorobenzoyl chloride and the yields of the reaction in each of the examples using different catalysts are given in Table 6.

TABLE 6

Acylation of benzene with 4-chlorobenzoyl chloride
Activity of various catalysts

| Examl. No. | Catalyst | % Conversion | % Yield |
|---|---|---|---|
| | Homogeneous Catalyst | | |
| 13 | Aluminium chloride | 90 | 70 |
| 14 | HPA (Dodecatungstophosphoric acid) | Nil | Nil |
| | Heterogeneous Catalyst | | |
| 15 | K-10 | Nil | Nil |
| 16 | HPA/K-10 | Nil | Nil |
| 17 | Filtrol | Nil | Nil |
| 18 | Indion 130 | Nil | Nil |
| 19 | Amberlyst-15 | Nil | Nil |
| 20 | Amberlite IR 120 | Nil | Nil |
| 21 | Sulphated Zirconia | 60 | 54 |
| 22 | UDCaT-1 | 82 | 75 |

It will be seen that none of these catalysts of examples 14–21 were active for this reaction. The catalyst of example 9 did not give yields better than that of AlCl$_3$ while example 22, using UDCaT-1 gave yield higher than that of AlCl$_3$ even though was poor. That shows less wastage.

It will be seen that the acylation reaction is very efficiently carried out with UDCaT-1 catalyst. Products were identified by IR spectra, $^1$H NMR, Melting point and purity by HPLC method.

The repeated runs were carried out by decanting the original contents of the reactor and later adding fresh reactants into the reactor. Care was taken that there was no loss of catalysts while the repeat experiments were carried out using the same used catalysts.

The results of these repeat experiments are given in Table 7.

TABLE 7

Acylation of benzene with 4-Chlorobenzoyl chloride
Repeat use of catalyst - UDCaT-1

| Runs | % Conversion | % Yield |
|---|---|---|
| First | 82 | 75 |
| Second | 81 | 75 |
| Third | 82 | 75 |

Examples 23–28

Alkylation of p-cresol with Methyl tert-butyl ether (MTBE).

It is well known that apart from its being a fuel oxygenate, MTBE has been employed as an excellent alkylating agent whereby only methanol would be a by-product of reaction. Butylated hydroxy toluenes (BHT) are among the well known industrial antioxidants and the basic raw materials for the manufacture of oil-soluble phenol formaldehyde resins that are conventionally prepared by the alkylation of p-cresol with isobutylene. BHT's are the usual source of isobutylene is the C$_4$ cut from the refineries. On cracking, MTBE gives high purity isobutylene. Further MTBE forms a homogeneous phase with p-cresol and thus monitoring the reaction becomes easier. The alkylation of p-cresol with MTBE has been studied with UDCaT-1 and has been found to give good activity.

Catalysts:

Filtrol-24, K-10, Indion-130 and HPA/K-10 were used. Filtrol-24 was obtained from Engelhard. K-10 was obtained from Fluka. Indion-130 used was a product of Ion Exchange (I) Ltd.

Chemicals:

p-Cresol was obtained from s.d. fine Chem(I) Ltd. MTBE was obtained from Texas Petrochemicals, USA. Other chemicals used were obtained from firms of repute.

Reaction procedure:

All experiments were carried out in a Parr Autoclave of 100 ml capacity equipped with a four blade pitched turbine impeller. The temperature was maintained at ±0.5° C. of the desired temperature. The instrument was also equipped with a speed regulator that could maintain the speed at ±5 rpm of the desired speed.

A predetermined quantity of reactants and the catalysts was charged into the autoclave and the temperature was raised to the desired value. Once the temperature was attained the initial sample was withdrawn which was the zero time sample. Further samples were drawn at periodic intervals.

A typical standard experiment contained 0.22 mole (19.61 g) of MTBE, 0.22 moles (24.31 g) of p-cresol and 3.5% w/w catalyst, based on reaction mixture. The temperature was maintained at 100° C. and the speed of agitation was 700 rpm.

Analysis:

The samples were analysed on a gas chromatograph (Perkin Elmer Model 8500) equipped with a flame ionisation detector. A 2 m×0.003 m column was used. The stationary phase was 10% OV-17 supported on chromosorb WHP. The GC conditions were as follows;

Carrier gas: Nitrogen

Carrier Flow: 20 ml/min

Inj. temperature: 300° C.

Det. Temperature: 300° C.

Oven conditions;

| Oven Temp 1 | Ramp | Oven Temp 2 | Ramp 2 | Oven Temp 3 |
|---|---|---|---|---|
| 40/2.5 min | 30 | 150/1.5 min | 30 | 270/2 min |

The quantitative analysis was done by comparison with standard synthetic mixtures.

Results:

Table 8 gives the % conversion of p-Cresol and selectivity to BHT with different types of catalysts. As from Table 8 UDCaT-1 is giving better conversion of p-cresol and selectively forming 2-tert-butyl-p-cresol.

TABLE 8

Activity of various catalysts for the alkylation of p-cresol with MTBE

| | Catalyst | % Conversion | % Selectivity |
|---|---|---|---|
| 23. | Filtrol-24 | 19 | 96 |
| 24. | Sul.Zirconia | 15 | 91 |
| 25. | K-10 | 12 | 96 |
| 26. | HPA/K-10 | 30 | 96 |
| 27. | Indion-130 | | |
| 28. | UDCaT-1 | 32 | 96 |

Examples 29–34

Friedel-Crafts alkylation of benzene/toluene with benzyl chloride

In these examples, Friedel-Crafts alkylation of benzyl chloride with benzene and toluene were carried out with classical $AlCl_3$, different bi-transition metals and UDCaT-1 as catalyst. Supported clays are the recent of the Friedel-Crafts alkylation catalysts reported to have exceptionally high activity for the reaction of benzyl chloride with benzene to give diphenylmethane. Diphenyl methane & diphenyl toluene are useful drug & pesticide intermediates, the reaction which uses the conventional $AlCl_3$ as the catalyst has several pollution problems & the reaction proceeds vigorously and is dangerous.

Chemicals:

Aluminium chloride and ferric chloride were obtained from s.d. Fine Chem Ltd. K-10 was obtained from Fluka. Benzene, benzyl chloride and toluene were products of s.d. Fine Chem Ltd.

Catalysts:

A bitransitional metal halide constituting of ferric chloride and aluminium chloride, HPA supported on K-10 were prepared as per UDCaT-1.

Aluminium chloride and ferric chloride supported in the ratios of 0:1, 1:3, 3:1, 1:0 were also prepared by the process described. UDCaT-1 was prepared as described under Example 13.

Experimental:

The reactor consisted of a flat glass vessel of 5 cm i.d. and 10 cm height equipped with baffles and a six blade impeller located at a height of 0.5 cm from the bottom. The assembly was kept in a water bath to maintain constant temperature. The reaction mixture could be agitated at the required speed with the help of a variable motor.

Reaction procedure:

All experiments were carried out by charging 39.50 mmol of benzyl chloride and 197 mmol each of benzene and toluene into the reaction vessel. Catalyst loading was 0.55 gm. The reaction was carried out at 45° C. Under such conditions 100% conversion was observed in 40 min. The reaction products are recovered by distillation. The products were diphenylmethane and benzyltoluene. The reaction was highly selective and no side products were formed.

Analysis:

Samples were analysed on a Chemito Gas Chromatography by using a ionisation detector and a spectrophysics integrator. For the analysis a S. S. column (94×3 mm) packed with OV-17 on chromosorb was used. The column conditions were maintained as follows. The quantitative analysis was done by calibrating with synthetic mixtures.

Results:

Conversion and Selectivity were shown in Table 9.

TABLE 9

Comparative activities of the supported catalysts.

| | Catalyst | Time (min) | % Conversion | Product selectivity (Benzyl benzene:Benzyl toluene) |
|---|---|---|---|---|
| 29. | K-10 | 45 | 6 | 1:4 |
| 30. | HPA/K-10 | 40 | 60 | 1:5 |
| 31. | $FeCl_3$/K-10 | 45 | 100 | 1:5.3 |
| 32. | $ZnCl_2$/K-10 | 40 | 45 | 1:4.3 |
| 33. | $FeCl_3$/$AlCl_3$/K-10 | 12 | 99 | 1:4.4 |
| 34. | UDCaT-1 | 45 | 98 | 1:5 |

The results show that between these catalysts UDCaT-1 is only the ecofriendly catalyst that gives conversion and selectivity similar to other non-ecofriendly catalysts.

Example 35–39

Vapour Phase Alkylation of Analine with tert-Butanol in the Presence of UDCaT-1.

Aniline is used as a building block for the manufacture of several products useful to the chemical industry. Aniline and its alkylated products are highly useful in fine chemical industry especially for the preparation of pharmaceuticals, drugs, pesticides, plastics, additives and dyes. Conventionally, Friedel-Crafts alkylation reactions are carried out with homogeneous acid catalysts used in stoichiometric quantities or in excess. The economics associated in the separation processes and the present day's stringent environmental concerns on the disposal of spent homogeneous catalysts make it difficult to proceed with them anymore. Heterogeneous acid catalysts have been employed in the synthesis of tert-butyl aromatic amines. They are usually prepared by reacting aniline over the acid catalysts with pure isobutylene or $C_4$ fraction from naphtha crackers, which contains isobutylene, under pressures ranging from 300–950 psig. (Burgoyne W. F. and Dixon D. D., *Applied Catalysis*, 63, (1990), 117.; Burgoyne W. F. and Dixon D. D., *Eur. Pat.* 336, 134, (October 1989), *C.A.,* 113 (1990): 171653w.; Frederick Harold H., *Eur. Pat.,* 69, 065, (January 1983), *C.A.,* 99 (1983): 38176u.; Lobanova N. S. and Popov M. A., *Zh. Prinkl. Khim.* (*Leningrade*), 43(4), (1970), 938. (Russ) *C.A.,* 73 (1970): 25032 g.). Reactions were performed by either co-feeding the arylamine and alkene over the solid catalyst in a fixed-bed reactor or by reacting the reagents and catalyst in a stirred autoclave.

In the presence of acid catalyst, tert-butanol cracks into isobutylene and water. Isobutylene thus produced reacts in situ with aniline giving different mono-alkylated products like n-tert-butylaniline, 2-tert-butylaniline, 4-tert-butylaniline and dialkylated products. We have now found that use of these novel mesoporous zeotype (UDCaT-1) catalyst for the Friedel-Crafts alkylation of aniline with tert-butanol, gives selectively 4-tert-butylaniline.

Catalysts:

$SO_4^{2-}$—$ZrO_2$ was prepared by the method given by Hino and Arata (Hino, M.; Arata, K. *J. Chem. Soc., Chem. Commun.,* 24, (1980), 851–852). HMS and UDCaT-1 were prepared as described under Example 1.

Chemicals:

All chemicals were procured from firms of repute. Tetraethyl orthosilicate (TEOS) (Fluka) was taken as the neutral silica source and dodecyl amine (Spectrochem Ltd.) as the neutral amine surfactant for the templates. Zirconium oxychloride, ammonia solution (AR grade), ammonium sulphate (AR grade), aniline (AR grade) and tert-butanol (AR grade) were procured from M/s, Loba Chemie and s.d. Fine Chemicals Ltd. respectively. Ethanol was purified by distillation and treatment with calcium oxide.

Reaction Procedure

The tert-butylation of aniline was carried out in a vapour phase fixed bed catalytic reactor at atmospheric pressure. 1.0 g of catalyst sample was placed in a tubular down flow glass reactor (40 cm×1.5 cm) and the catalyst section was packed between two sections of glass wool. The reactants mixed in a proper ratio were fed from the top by using a calibrated motorised syringe pump. Glass beads loaded at the top of the catalyst bed were used as pre-heating zone. Nitrogen was used as the carrier gas and the flow rate was controlled by a rotameter at a range of 15 ml/min and 30 ml/min. It was calibrated carefully with a soap film meter in every run. Examples 35–39 were carried out using different catalyst at feed rates and temperature region as given below in the Table 10. The liquid products were obtained by circulating cold water through the condenser. Aniline was separated by distillation and the product 4-tert-butylaniline was obtained.

In example 39, a run of 3 hrs gave 10 g of aniline and 4-tert-butylaniline mixture. On distillation it gave 2.5 g of 4-tert-butylaniline.

Analysis of Reaction Mixture

The products were analysed by gas chromatography (Model Chemito 8510) using 4 m×3 mm i.d., stainless steel column packed either with 5% SE-30 or OV-17 on chromosorb WHP, coupled with a flame ionisation detector. Synthetic mixtures of reactants and products were used to calibrate the G.C. results for quantification. A typical mass spectral fragmentation pattern of alkylated product proves that the product obtained is mono alkylated product. The $^1H$ NMR (500 MHz) spectra shows that the product formed is 4-tert-butyl aniline.

The mass spectral fragmentation pattern of aniline alkylation reaction mixture confirming the mono alkylation. The separated product was then further analysed by $^1H$ NMR for its mono alkylation. $^1H$ NMR (500 MHz) using $CDCl_3$, $\delta 7.25$ (d, J=8.514 Hz, 2H), $\delta 6.7$ (d, J=8.483, 2H), $\delta 3.78$ (s, 2H), $\delta 1.35$ (s, 9H) spectra shows that the product formed is 4-tert-butyl aniline. Thus N-alkylation was totally absent using UDCaT-1 whereas it was a major product in the case of DTP/K-10 as a catalyst as reported elsewhere (Doshi N. S., *Ph.D. Thesis*, University of Mumbai., 1998). The reaction results are summarised in Table 10.

Results:

Table 10 gives the % conversion of aniline and selectivity to 4-tert-butyl aniline with different types of catalysts. As from Table 10 UDCaT-1 is giving better conversion of aniline and selectivity forming 4-tert-butyl aniline.

TABLE 10

Alkylation of aniline with tert-butanol

| Ex. No. | Catalyst | Conversion (%) | Selectivity (%)[c] |
|---------|----------|----------------|--------------------|
| 35. | HMS | <1 | — |
| 36. | $ZrO_2$ | <1 | — |
| 37. | $SO_4^{-2}$—$ZrO_2$ | 5 | 98 |
| 38. | UDCaT-1[a] | 20 | 99 |
| 39. | UDCaT-1[b] | 30 | 99 |

Reaction Conditions = Aniline and tert-butanol were taken in 1:4 mole ratio, Catalyst loading = 1 g., Reaction temperature = 250° C., Reactant feed rate = 6.5 ml/h.
[a]Nitrogen flow rate = 30 ml/min.
[b]Nitrogen flow rate = 15 ml/min.
[c]4-tert-butylaniline.

Examples 38 and 39 show high conversion and high selectivity.

In continuous processes the isobutylene vapours can be recirculated and yields should be high.

We claim:

1. A highly acidic mesoporous synergistic solid catalyst, said catalyst:
    comprising hexagonal mesoporous silica having sulphated metal oxide of metal selected from the group consisting of zirconium, titanium, iron, aluminium, tin and bismuth incorporated therein, and
    having a surface area in the range 200–500 $m^2/g$; a pore volume in the range of 0.1–0.3 ml/g; a pore diameter in the range of 25–35 Å and XRD peak at 2 theta angle being 0–3.

2. A highly acidic mesoporous synergistic solid catalyst as claimed in claim 1, having elemental constitution of silicon (Si) 50–60 wt %, zirconium (Zr) 40–50 wt % and sulphur (S) 5–10 wt %.

3. A highly acidic mesoporous synergistic solid catalyst as claimed in claim 1, wherein said hexagonal mesoporous silica is prepared from alkoxide of silicon with primary amine as a template, the said primary amine having from 8 to 16 carbon atoms.

4. A highly acidic mesoporous synergistic solid catalyst as claimed in claim 1, wherein said sulphated metal oxide comprises zirconium oxychloride.

5. A process for producing a highly acidic mesoporous solid catalyst comprising hexagonal mesoporous silica having sulphated metal oxide of metal selected from the group consisting of zirconium, titanium, iron, aluminium, tin and bismuth incorporated therein, and having a surface area in the range 200–500 m$^2$/g; a pore volume in the range of 0.1–0.3 ml/g; a pore diameter in the range of 25–35 Å and XRD peak at 2 theta angle being 0–3, said process comprising:
(i) depositing water soluble salts of metals in an amount of 0.1–5.0 parts by weight into hexagonal mesoporous silica (HMS) with a pore size >13 Å in an amount of 1–10 parts by weight;
(ii) passing ammonia gas over the metal salt deposited HMS and thereby converting the metal salt deposits in the HMS to metal hydroxide deposits in HMS, followed by washing and drying either under vacuum at 50–100° C. or at 100–150° C. at atmospheric pressure;
(iii) sulphating the metal hydroxide deposits in the HMS with at least one sulphating agent; and
(iv) calcining the sulphated, metal deposited HMS between 400–700° C. to thereby obtain the said catalyst.

6. A process as claimed in claim 4, wherein said calcining is carried out at between 500 and 700° C.

7. A process for producing a highly acidic mesoporous solid catalyst as claimed in claim 4, wherein said sulphating agent(s) are selected from sulphuric acid, ammonium sulphate, sulphur dioxide, sulphur trioxide and hydrogen sulphide.

8. A process for producing the highly acidic mesoporous solid catalyst as claimed in claim 4, wherein the dried metal salt containing HMS is provided in a vertical vapour phase reactor and ammonia gas is passed through it for 1–3 h which is dried at 80–150° C. for 1–3 h to obtain said metal hydroxide deposited HMS.

9. A process for producing the highly acidic mesoporous solid catalyst as claimed in claim 4, wherein the sulphation of the metal hydroxide deposited HMS is carried out by treatment with at least one of said sulphating agents either in solution or in gaseous phase.

10. A process for producing the highly acidic mesoporous solid catalyst as claimed in claim 4, wherein the said HMS is obtained following dissolving a primary amine as the template in an aqueous alcohol mixture; adding an alkoxide of silicon under vigorous stirring; allowing the reaction mixture to age for 5–30 h at a temperature of up to 100° C.; separating the precipitate and drying, and calcining at a temperature between 400° C. and 700° C. to thereby obtain said HMS.

11. A process for producing oligomers from alpha-olefins using a catalyst comprising hexagonal mesoporous silica having sulphated metal oxide of metal selected from the group consisting of zirconium, titanium, iron, aluminium, tin and bismuth incorporated therein, and having a surface area in the range 200–500 m$^2$/g; a pore volume in the range of 0.1– 0.3 ml/g; a pore diameter in the range of 25–35 Å and XRD peak at 2 theta angle being 0–3, the process comprising:
contacting alpha olefin feedstock, RCH=CH$_2$ wherein R represents an alkyl radical having 6 to 12 carbon numbers with said catalyst;
adding 1 to 10% by weight of alpha olefin, under agitation;
raising the temperature to 120 to 220° C. in autoclave, appropriate to the hydrocarbon(s) in the feedstock and maintaining the reaction at that temperature under agitations for a period between 2 to 10 hours under pressure;
cooling the autoclave to room temperature and separating the solid catalyst from the liquid products of the reaction followed by separating the unreacted monomer and the oligomer.

12. A process as claimed in claim 11, wherein said unreacted monomer and the oligomer are separated by distillation under vacuum.

13. A process as claimed in claim 11, wherein said alpha olefin feed stock and said sulphated metal oxide incorporated hexagonal mesoporous silica is contacted in an autoclave.

14. A process as claimed in claim 11, wherein the oligomerisation reaction is controlled to a dimer stage.

15. A process for Friedel-Crafts reactions using a catalyst comprising hexagonal mesoporous silica having sulphated metal oxide of metal selected from the group consisting of zirconium, titanium, iron, aluminium, tin and bismuth incorporated therein, and having a surface area in the range 200–500 m$^2$/g; a pore volume in the range of 0.1–0.3 ml/g; a pore diameter in the range of 25–35 Å and XRD peak at 2 theta angle being 0–3, wherein said process comprises:
i. contacting aromatic compounds with acylating/alkylating agent in the presence of said catalyst;
ii. maintaining the reaction under stirring at the reaction temperature 50–100° C. from 30 mins to 6 hours; and
iii. recovering the reaction product.

16. Process as claimed in claim 15, wherein said aromatic compound used is the following formula

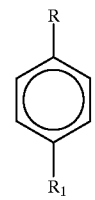

wherein R and R$_1$ are as follows:
when R=H, R$_1$=H and
when R=CH$_3$, R$_1$=O or H.

17. Process as claimed in claim 15, wherein said acylating agent used is 4-chlorobenzoyl chloride.

18. Process as claimed in claim 15, wherein said alkylating agent used is selected from methyl tert-butyl ether (MTBE) and benzyl chloride.

19. Process as claimed in claim 15, wherein said catalyst is used in an amount of 1.5%–15% w/w of the reaction mixture.

20. Process as claimed in claim 15, wherein said catalyst is reused for carrying out the next batch of the same reaction.

21. A process for the vapour phase reaction for alkylating arylamine selectively at the para-position using a catalyst comprising hexagonal mesoporous silica having sulphated metal oxide of metal selected from the group consisting of zirconium, titanium, iron, aluminium, tin and bismuth incorporated therein, and having a surface area in the range 200–500 m$^2$/g; a pore volume in the range of 0.1–0.3 ml/g; a pore diameter in the range of 25–35 Å and XRD peak at 2 theta angle being 0–3, wherein said process comprises:
i) contacting arylamines with an alkylating agent both in vapour phase in the presence of said catalyst;

ii) maintaining the reaction temperature between 150–400° C. in the tubular down flow reactor;

iii) recovering the reaction product.

22. A process as claimed in claim 21, wherein said arylamine is selected from the group comprising, aniline, alkylated anilines, halogenated anilines, hydroxylated anilines.

23. A process as claimed in claim 22, wherein said arylamine is aniline and said alkylating agent is tert-butanol.

24. A process as claimed in claim 22, wherein the ratio of the arylamine to alkylating agent is between 4:1 to 1:10.

25. A process as claimed in claim 21 wherein said alkylating agent is selected from a group comprising alkanols with a carbon number from $C_2$ to $C_{16}$, cyclic alcohols such as cyclohexanol and olefins comprising ethylene, propylenes, butylenes, isoamylene, cyclohexene, and other α-olefins.

* * * * *